United States Patent [19]

Clendining

[11] Patent Number: Plant 6,827

[45] Date of Patent: Jun. 6, 1989

[54] PEACH TREE

[75] Inventor: Ed Clendining, Sewell, N.J.

[73] Assignee: Adams County Nursery Inc., Aspers, Pa.

[21] Appl. No.: 166,244

[22] Filed: Mar. 10, 1988

[51] Int. Cl.[4] ..... A01H 5/00

[52] U.S. Cl. ..... Plt./43

[58] Field of Search ..... Plt. 43

*Primary Examiner*—Robert E. Bagwill

*Attorney, Agent, or Firm*—Frank B. Robb

[57] ABSTRACT

There is disclosed a new and distinct peach variety which originated as a natural limb mutation of the unpatented variety Loring, and is a peach tree which produces early midseason maturing, yellow-fleshed, semi-freestone peaches, which are large, round, firm and have an attractive bright red skin color, which color covers seventy to eighty percent of the surface of the fruit when fully mature, the flesh being golden yellow with a rich, delicious flavor.

1 Drawing Sheet

BACKGROUND OF THE INVENTION

My new and distinct variety originated as a natural limb mutation of the variety Loring. The variety was observed because of its bright and almost complete red skin color and because the fruit matured two weeks before Loring.

Budwood was collected and budded on peach seedling rootstock in Aspers, Pa. in August.

Buds grown during the summer provided finished trees dug for planting in the spring of the next year. A group of trees were planted near Richwood, N.J. and the characteristics used as a basis for selection were observed from year to year thereafter, establishing that they are true and continuing. Trees were planted near Richwood, N.J. and the characteristics used as a basis for selection were observed from year to year thereafter, establishing that they are true and continuing.

Trees of this variety exhibit the strong vigorous, upright spreading growth habit which is characteristic of Loring. It also appears to have the regular but somewhat light bearing habit of Loring. Fruit of this variety are similar to Loring. However my new variety matures two weeks ahead of Loring and one week ahead of another Loring mutation U.S. Plant Pat. No. 4,170.

It is definitely different from the two varieties referred to because of its significantly greater and more complete scarlet to crimson skin color than U.S. Plant Pat. No. 4,170 and its maturity two weeks ahead of Loring.

My new variety has similar susceptibility to major peach diseases as the Loring variety.

The flowers of this new variety are similar in size, shape, color, and time of bloom to the variety Loring.

Asexual propagation of my new variety has demonstrated that its combination of characteristics comes true to form and is established and transmitted through succeeding generations.

In the accompanying illustration, there is shown typical specimens of the fruit and foliage of my new variety as depicted in color as nearly true as is reasonably possible to make the same in a color illustration of this character, color references being those to the Nickerson Color Fan.

DETAILED DESCRIPTION OF THE NEW VARIETY

Dates of first and last pickings: July 22 and August 3.

Tree: Large size; vigorous, open, upright-spreading, vase formed, half hardy, medium productive, regular bearer.

*Trunk.*—Medium smooth.

*Branches.*—Medium smooth; grayish brown, medium glossy. Lenticels — Medium small.

*Leaves.*—Length — 7 to 7.5 inches. Width — 1.25 to 1.75". Color — Moderate olive green 5GY4/3. Margin — Crenate. Petiole — Long medium; slender. Glands — Average number 3; opposite; medium, globose.

Flowers:

*Date of first blossoms.*—March 30 and full blossoms, April 2; early.

*Size.*—Large.

*Color.*—Strong pink 10RP 7/8.

Fruit:

*Maturity when described.*—Hard; under-ripe; date — July 30.

*Size.*—Large. Axial diameter 2.50 to 3.25". Transverse in suture planes 2.63 to 3". At right angles to suture planes 2.66 to 3".

*Form.*—Variable; globose to very slightly oblong.

*Suture.*—Very distinct; extends from base to beyond but discontinues at apex over entire circumference; has slight marked depression beyond pistil point.

*Ventral surface.*—Rounded; slightly ridged on either side.

*Cavity.*—Rounded.

*Base.*—Retuse.

*Apex.*—Mamiform.

*Stem.*—Short length; pubescent; medium.

*Skin.*—Medium; free. Color — Highly blushed deep reddish orange covering 70% to 80% of surface. 7.5R 4/11. Speckled reddish orange reds to an orange yellow 10YR 7/10.

*Flesh.*—Color — Yellow; streaked; with red next to skin and stone. Surface of pit cavity — Yellow fibres. Amygladin — Scant. Texture — Firm; melting. Fibres — Few; fine. Ripens — Fairly even. Flavor — Mild; delicate. Aroma — Wanting. Eating quality — Good.

Stone: Semi-free.

*Fibers.*—Parts from flesh smoothly when ripe.

*Size.*—Medium.

*Length.*—1.25 to 1.50".

*Thickness.*—1.62 to 1.25".

*Form.*—Oblong.

*Base.*—Hilum.

*Apex.*—Rounded to acuminate.

*Sides.*—Equal.

*Surface.*—Furrowed near base.

Use: Multiple uses.

Keeping quality: Medium.

Resistance to insects: Good; no bacterial spot.

Resistance to diseases: Medium.

Shipping quality: Good.

I claim:

1. A new and distinct variety of yellow freestone peach tree, substantially as illustrated and described, characterized as to novelty by its strong vigorous growth habit, regular productivity and the ability to yield large, round, firm, globose, deep and fully red colored peaches with a rich and delicious flavor, ripening two weeks before Loring.

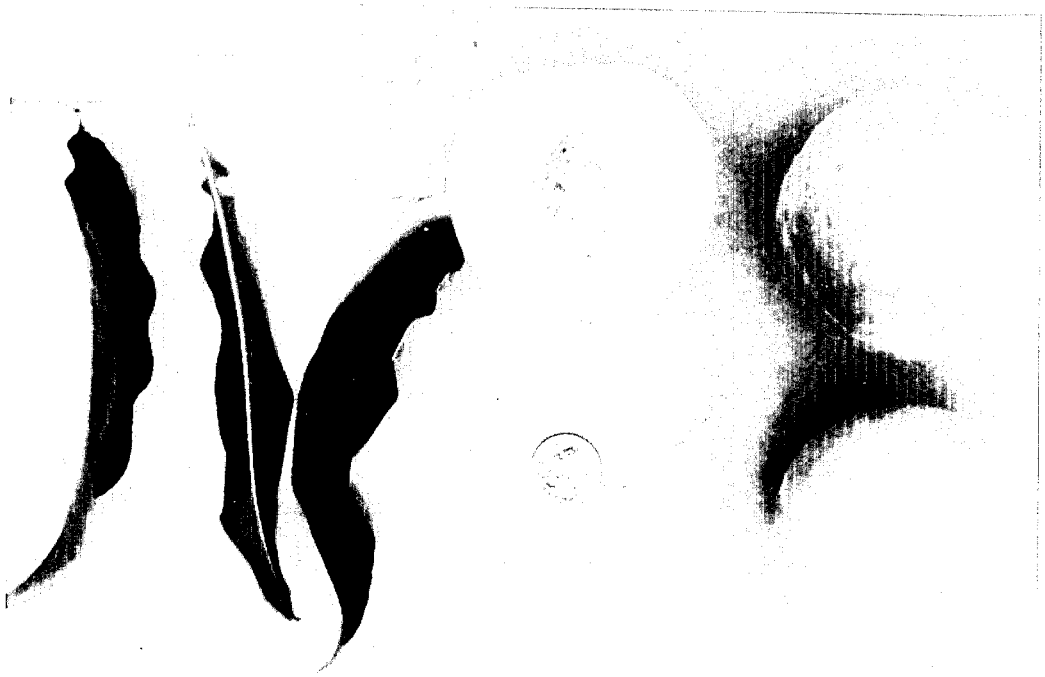

* * * * *